United States Patent [19]
Calderon

[11] Patent Number: 5,316,477
[45] Date of Patent: May 31, 1994

[54] UNIVERSAL IMPLANT ABUTMENT

[76] Inventor: Luis O. Calderon, 8522 S.W. 74 St., Miami, Fla. 33143

[21] Appl. No.: 66,269

[22] Filed: May 25, 1993

[51] Int. Cl.$^5$ .............................................. A61C 8/00
[52] U.S. Cl. ..................................... 433/173; 433/172
[58] Field of Search ........................ 433/172, 173, 174

[56] References Cited

U.S. PATENT DOCUMENTS

| | | | |
|---|---|---|---|
| 4,842,518 | 6/1989 | Linkow et al. | 433/174 |
| 4,907,969 | 3/1990 | Ward | 433/173 |
| 4,975,059 | 12/1990 | Sendax | 433/173 |
| 5,030,095 | 7/1991 | Niznick | 433/173 |
| 5,035,619 | 7/1991 | Daftary | 433/174 |
| 5,116,225 | 5/1992 | Riera | 433/173 |

OTHER PUBLICATIONS

Articles by Andre Schroeder et al. The New Concept of ITI Hollow-Cylinder and Hollow-Screw Implants, Parts 1 and 2 of vol. 3, No. 3, 1988, The Int'l Journal of Oral and Maxillofacial Implants.
Catalog of the Core-Vent Corporation, pp. 13,16 and 18, 1991.
Brochure issued by "O" Company, Inc., Albuquerque, N.M. pp. 1 and 7.

*Primary Examiner*—John J. Wilson
*Attorney, Agent, or Firm*—Jay Sanchelima

[57] ABSTRACT

The improvement of the present invention pertains to a frustoconical abutment intended to overcome the problem of the implant's lack of parallelism. The abutment can be of the Allen-driven type or the through-screw type. Both engage with an implant ranging from partially to totally inserted below the gingival margin. The abutment of the Allen-driven type includes a threaded cavity that receives a threaded member of a prosthesis. The through-screw abutment includes a threaded through-opening that also receives the threaded member of a prosthesis. The frustoconical abutment permits a dentist to reduce the mass to end up with a resulting shape that will correct the lack of parallelism typically created by misaligned implants and allowing for more aesthetic form which mimics a natural tooth shape. This is particularly helpful when part of the implant's end protrudes from the gingival margin instead of submerged below it.

8 Claims, 3 Drawing Sheets

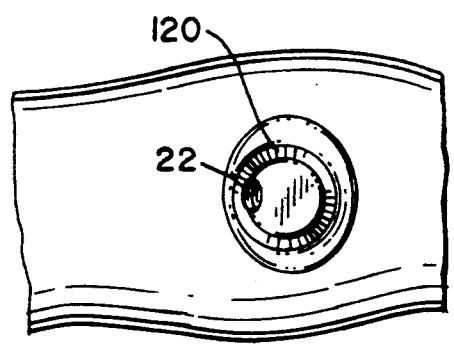
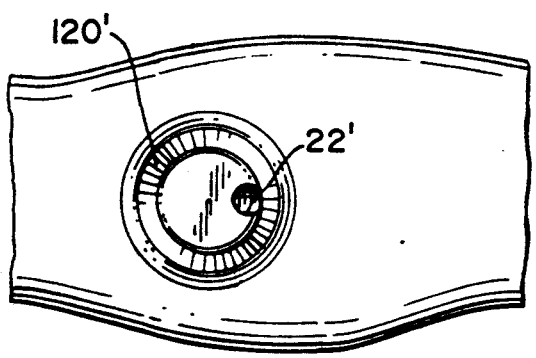
FIG - 10.    FIG - 11.
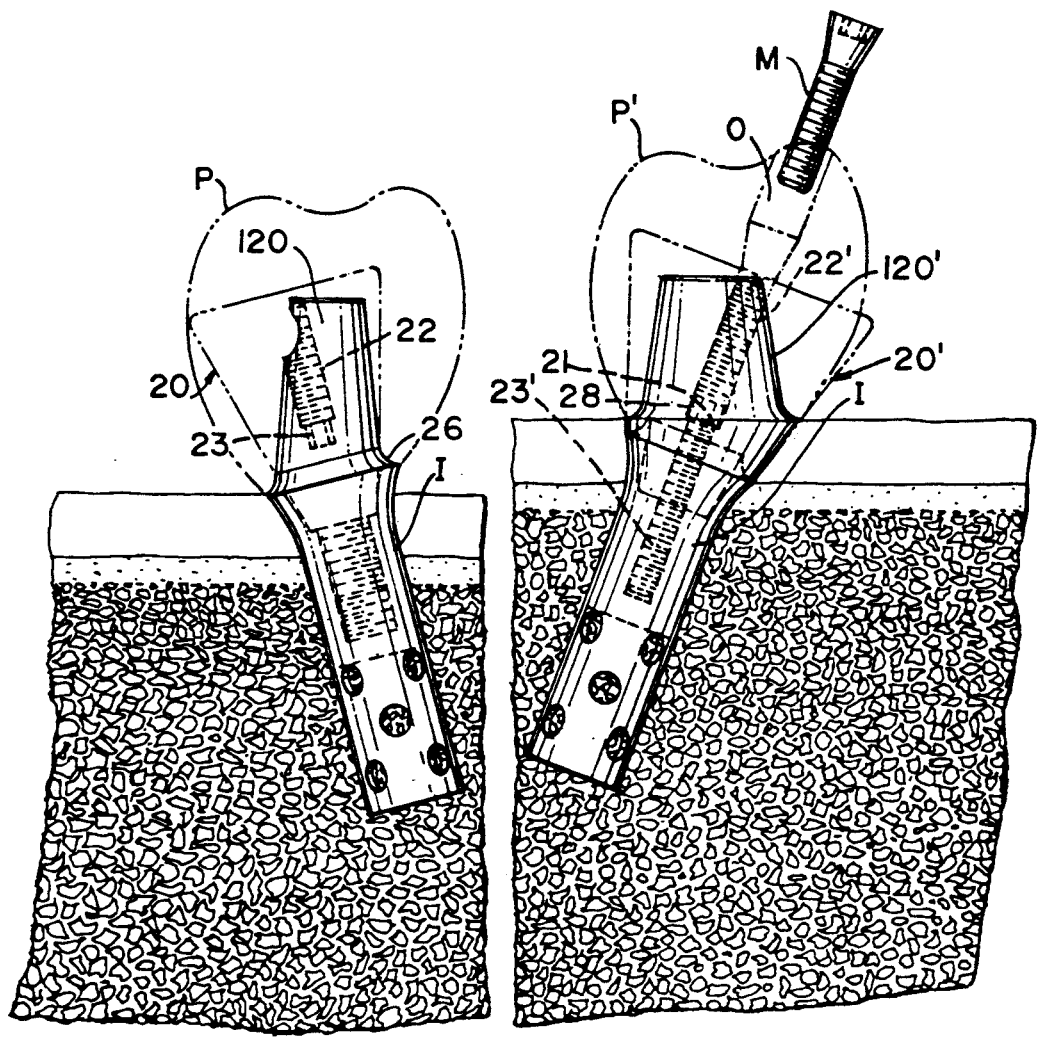
FIG - 10A.    FIG - 11A.

UNIVERSAL IMPLANT ABUTMENT

BACKGROUND OF THE INVENTION

1. Field of the Invention

The present invention relates to dental implants which replace natural teeth, particularly to be used as support for oral restorative prostheses which include crowns, fixed partial dentures, removable partial dentures, or full dentures.

2. Description of the Related Art

Dental implants to replace natural teeth comprise basically three components. First, the implant, which is surgically placed into the mandibular and/or maxillary bone. Second, the abutment, which is mounted on the implant after bio-integration of the implant and which serves as a retainer for the prosthesis. Third, the oral restorative prosthesis, which is placed over the implant abutment. One of the latest implant techniques involves the use of hollow-cylinder and/or hollow-screw implants. See articles by Andre Schroeder et al, The New Concept of ITI Hollow-Cylinder and Hollow-Screw Implants, Parts 1 and 2 of Volume 3, Number 3, 1988, The International Journal of Oral and Maxillofacial Implants. A basic concept of parallelism with respect to the existing teeth, or in this case implants, must exist. This invention allows for proper path of insertion or retrievability of the prosthesis over the supporting structure (whether a natural tooth or an implant). The problem which many times arises is that the implant cannot be placed in a substantially parallel relationship to other existing teeth or implants. Therefore, the correction for this parallelism defect must be addressed at the time of mounting the abutment to allow proper prosthetic insertion and retrievability.

At this time, many implant manufacturers attempt to solve this problem by producing many different specific components as documented in the attached product catalog of the Core-Vent Corporation, page 13. A large variety of these abutments exist, but they address only a few very specific situations. When it becomes necessary to change these abutment shapes in order to resolve the specific problem of lack of parallelism, the following process takes place: (a) modifying either a gold-coping abutment or acrylic pattern for an abutment by cutting it down to the appropriate shape; (b) wax or acrylic is then added to modify the structure; (c) when correct parallelism is achieved, the abutment is then cast in gold, and adapted to the existing implant. This results in implant manufacturers having to offer several different abutments to try to overcome the lack of correct angulation, and requires extensive time and work from the dentist in adapting it to the existing situation.

One approach to correct the lack of parallelism is to provide an abutment with a set screw as documented on page 7 of the brochure issued by "O" Company, Inc., Albuquerque, N. Mex., a copy of which is attached hereto. However, this approach requires the use of two screws or threaded members (one at the bottom of the abutment to engage the implant and the other one being the set screw) with the consequent mechanical instability. Also, this approach does not permit an accurate anatomical adaptation of the abutment in the area of the free gingival margin. The abutment in the present invention can be worked more easily and with more flexibility, specially when the implant's abutment receiving end is partially or totally submerged in the gingiva (gum). Also, the prior art approach does not permit a dentist to work directly to correct the lack of parallelism if the latter exceeds fifteen degrees. Finally, this approach requires a dentist to keep a large inventory of abutments and components with different degrees of inclination.

Up to now, all implants have a circular cross-section. The point where the prosthesis and the implant attach also has a circular projection. This is not true with the natural teeth that implants are replacing. Usually, the prosthesis over a natural tooth rests over a structure which has a non-circular natural diameter. Therefore, the circular implants and abutments of the prior art are limited in their ability to reproduce anatomical characteristics of natural teeth thereby limiting the desired aesthetic characteristics of the prosthesis.

SUMMARY OF THE INVENTION

It is one of the main objectives of the present invention to provide a universal implant abutment to readily correct the lack of parallelism in implants.

It is still another objective of this invention to eliminate complicated and time-consuming steps, like creating abutment patterns in order to adapt to a specific situation, having to build up needed structure by adding wax or acrylic, or making a die in order to cast the custom-made abutment so it can be mounted to the implant in a way that can be readily removed.

It is yet another object of this invention to provide such a device that is simple and inexpensive to manufacture while retaining its effectiveness.

By using this invention, the dentist will simply cut away any unnecessary structure on the abutment, only leaving the necessary structure that will obviate the parallelism problem. This can be done with the abutment mounted to the implant, or unmounted. No additional structure will need to be added, saving much time, expense, and additional work.

With this invention the dentist is also able to shape the abutment to reproduce more closely the shape of the natural tooth at the gum line level. This increases the aesthetic characteristics for the prosthesis.

Further objects of the invention will be brought out in the following part of the specification, wherein a detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 10 corresponds to a top view of the frustoconical abutment of the Allen-driven type.

FIG. 10A represents a side elevational view of an implant with a frustoconical abutment of the Allen-driven type represented with dotted lines as it originally was and with solid lines for the resulting abutment. The implant's abutment receiving end is not submerged below the gingival margin.

FIG. 11 corresponds to a top view of the frustoconical abutment of the through-screw type.

FIG. 11A represents a side elevational view of an implant with a frustoconical abutment of the through-screw type represented with dotted lines as it originally was and with solid lines for the resulting abutment. The implant's abutment receiving end is partially submerged below the gingival margin.

DETAILED DESCRIPTION OF THE PREFERRED EMBODIMENT

Figure 1:
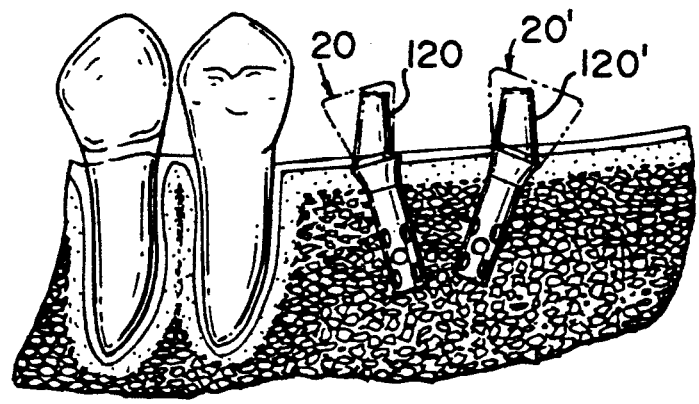
FIG. 1 shows an elevational view of two implants in position in a jaw bone next to two natural teeth and the implants showing the original frustoconical abutment in phantom and the resulting reduced abutment, in substantial parallel spaced apart relationship to each other, in solid lines.
Figure 2:
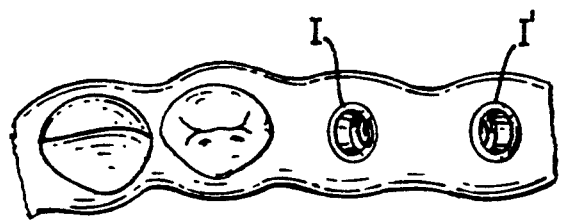
FIG. 2 is a top view of FIG. 1 where the abutments have been removed.
Figure 3:
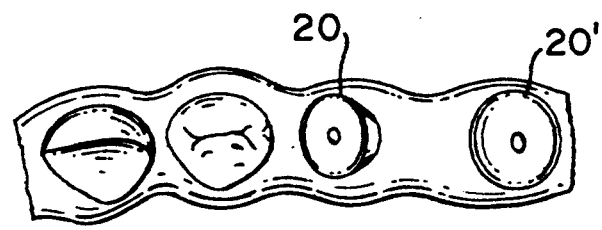
FIG. 3 is also a top view like FIG. 2 with the unworked frustoconical abutments mounted on the implants.

As it can be seen from the drawings, the present invention pertains to an improvement over the existing abutments that are cooperatively received by implants and the improvement is intended to provide a parallel anchorage support for the prostheses to be used.

In FIGS. 1; 5 and 8 implant I has been represented and it corresponds to the one used and described in the above referenced publications. Implant I typically comes with chamfer 26 and 26'. Abutment 20 and 20' correspond to frustoconical abutments designated as the Allen-driven and through-screw types, respectively. Different from the abutments described in the prior art, abutments 20 and 20' have a frustoconical shape that permit the cutting away of unnecessary mass to end up with 120 and/or 120' as shown in FIG. 10A and 11A.

Figure 4:
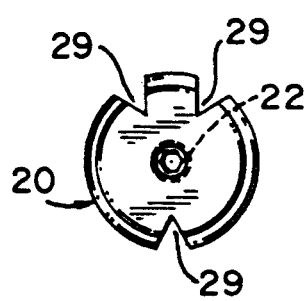
FIG. 4 corresponds to a top view of the frustoconical abutment with a centrally disposed screw cavity to cooperatively receive an Allen-shape cavity to receive an Allen wrench to impart the rotational torque necessary to screw and unscrew the abutment to the implant.
Figure 7:
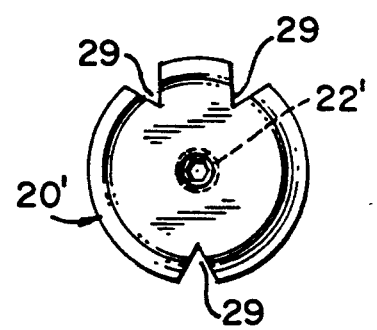
FIG. 7 corresponds to a top view of the frustoconical abutment of the through-screw type.

Incisions 29 are intended to provide a reference mark for abutments 20 and 20', as best shown in FIGS. 4 and 7. This is useful when the indirect method for working on the abutments is used so that when the abutment is worked on outside the patient's mouth, in a working cast, the dentist will have a reference of its location in the working impression.

Figure 5:
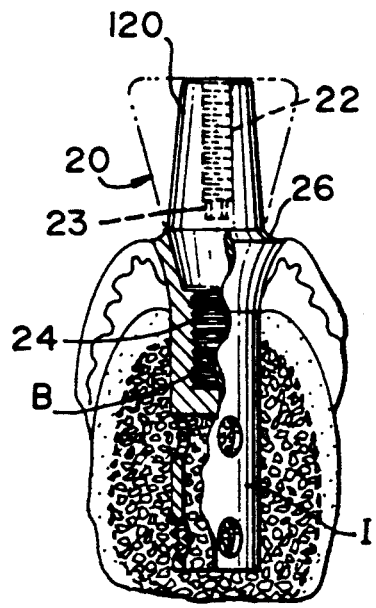
FIG. 5 represents a partial cross-sectional elevational view of the implant and the resulting abutment with solid lines with the screw cavity shown with dotted lines and the Allen-shaped cavity at the bottom of the screw cavity.
Figure 8:
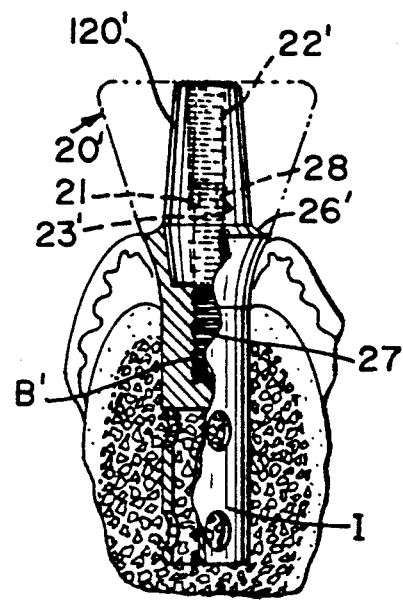
FIG. 8 is a partial cross-sectional elevational view of the frustoconical abutment of the through-screw type after being reduced and the unworked abutment shown in phantom.
Figure 6:
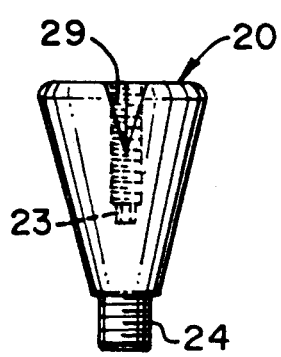
FIG. 6 shows an elevational side view of the frustoconical abutment of the Allen-driven type.
Figure 9:
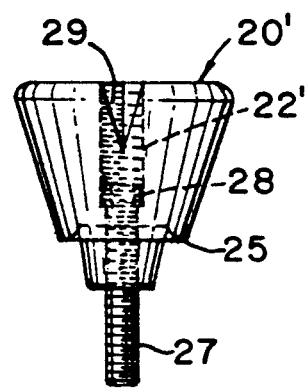
FIG. 9 shows an elevational side view of the frustoconical abutment of the through-screw type with the screw mounted therein and partially protruding outwardly.

Abutment 20 is characterized by the centrally disposed longitudinal threaded cavity 22 designed to cooperatively permit an Allen wrench through and provides a cooperating thread for engaging the threaded terminations of the prosthesis P that will be mounted on abutment 120. For the purposes of this application, we will use numeral 20 to refer to the unworked abutment and numeral 120 to refer to the abutment after being worked and adapted. Allen-shape cavity 23 is formed at the bottom of cavity 22 to cooperatively receive an Allen wrench to apply the necessary torque to screw or remove the abutment 20. Cavity 22 extends a sufficient distance inside abutment 20 so that the cutting of lateral walls of abutment 20 does not adversely affect the effective length of threaded cavity 22. Threaded cavity 22 is intended to receive cooperating screw members from additional restoration pieces that may be needed. In FIG. 5, abutment 120 has a screw terminal 24 that is cooperatively received by threaded bore B in implant I. Prosthesis P is cemented on abutment 120 in FIG. 10A.

Abutment 20' is characterized by having a threaded centrally disposed counterbore opening 22' and threaded opening 23' through which a screw 27 passes and is cooperatively received by threaded opening B' of implant I'. Counterbore opening 22' has a larger diameter than threaded opening 23' so that a recessed surface 21 is defined for receiving head 28 of screw 27. Abutment 20' includes skirt member 25 and when the former one is screwed all the way in, the latter comes in contact with chamfer 26' of implant I'. Prosthesis P' includes threaded member M that goes through opening O and cooperatively engages with threaded cavity 22' as shown in FIG. 11A. It should be noted, that the prosthesis P' (having a threaded member M) can also be used with abutment 20 of the Allen-type.

Both abutments, 20 and 20', have lateral frustoconical walls at a maximum angle of approximately 30 degrees with respect to their longitudinal axis. If the implant is positioned at an angle greater than 30 degrees, the correction using the present device is not possible and, more than likely, the implant procedure needs to be redone because excessive lateral occlusal forces would result.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. In an abutment that cooperatively supports a prosthesis and engages with an implant of the cylindrical type, said implant being positioned inside the maxillary and mandibular bones in a substantially perpendicular relationship thereto and said implant further including a threaded central opening, and said abutment comprising anchorage means for mounting said prosthesis thereon the improvement comprising a frustoconical shape for said abutment having the narrower portion adjacent to said implant so that sufficient mass is provided to permit a user to cut away portions of said abutment to correct the lack of parallelism of said implant.

2. The improvement set forth in claim 1 wherein said frustoconical abutment includes a lateral wall extending at an angle with respect to the longitudinal axis of said frustoconical abutment of at least 15 degrees and approximately no more than 30 degrees.

3. The improvement set forth in claim 2 wherein said abutment includes a threaded end rigidly mounted thereto and further includes means for permitting the application of sufficient torque to said frustoconical abutment to make said threaded end advance and retreat along said threaded central opening.

4. The improvement set forth in claim 3 wherein said means for permitting the application of sufficient torque to said frustoconical abutment includes a centrally disposed cavity that extends longitudinally along said abutment, having a bottom, and said bottom has a cooperating shape to receive a suitable wrench to impart said torque.

5. The improvement set forth in claim 4 wherein said cavity includes an internal thread and said prosthesis includes a mating threaded member for cooperative engagement with said threaded cavity.

6. The improvement set forth in claim 5 wherein the shape of said bottom corresponds to an Allen configuration.

7. The improvement set forth in claim 2 wherein said anchorage means for mounting a prosthesis includes a threaded through-opening longitudinally extending along and through said abutment and said threaded through-opening having a counterbore opening so that a recessed surface is defined, and said implant further includes through-screw means cooperatively and matingly received by said threaded through-opening and said screw means including a head that cooperatively engages with said surface so that abutment is urged towards said implant as said screw means is advanced through said threaded through-opening.

8. The improvement set forth in claim 7 wherein said implant includes a chamfer on the portion protruding outside the jaw bone and said abutment ends with a skirt member that comes in cooperative contact with said chamfer so that sufficient mass of said abutment extends outwardly to permit the correction of the lack of parallelism introduced by said implant by providing a resulting mass that comes up to the gingival margin where the implant is below the gingival margin.

* * * * *